United States Patent
Buser et al.

(10) Patent No.: US 6,284,869 B1
(45) Date of Patent: Sep. 4, 2001

(54) ADDUCT OF AN EPOXY COMPOUND AND CYCLIC PHOSPHITE

(75) Inventors: Antonius Johannes Wilhelmus Buser, DA Wehl; Jan André Jozef Schutyser, JJ Dieren, both of (NL)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 09/254,076
(22) PCT Filed: Aug. 6, 1997
(86) PCT No.: PCT/EP97/04406
§ 371 Date: Jun. 14, 1999
§ 102(e) Date: Jun. 14, 1999
(87) PCT Pub. No.: WO98/07731
PCT Pub. Date: Feb. 26, 1998

(30) Foreign Application Priority Data

Aug. 23, 1996 (NL) .................................................. 1003863

(51) Int. Cl.[7] .............................. C08G 79/02; B32B 3/00
(52) U.S. Cl. ........................ 528/398; 528/108; 428/209; 428/901
(58) Field of Search ................................ 528/398, 108; 428/209, 901

(56) References Cited

U.S. PATENT DOCUMENTS

| | | | |
|---|---|---|---|
| 3,298,967 | * 1/1967 | Mason | 528/398 |
| 3,328,319 | * 6/1967 | Galinke | 528/108 |
| 3,399,171 | 8/1968 | Vogt et al. . | |
| 3,971,813 | 7/1976 | Porret et al. . | |
| 4,316,006 | * 2/1982 | McEwen | 528/398 |
| 4,716,185 | * 12/1987 | Rabener | 528/398 |
| 5,900,469 | * 5/1999 | Kleiner et al. | 528/108 |

FOREIGN PATENT DOCUMENTS

| | | |
|---|---|---|
| 456949 | 7/1968 | (CH) . |
| 4221678 | 1/1994 | (DE) . |
| 1503429 | 11/1967 | (FR) . |
| 46/20824 | 6/1971 | (JP) . |
| 93/10936 | 6/1993 | (WO) . |

OTHER PUBLICATIONS

Bärbel Überlacker et al., "Ectopic Expression of the Maize Homeobox Genes ZmHoxla or ZmHoxlb causes Pleiotropic Alterations in the Vegetative and Floral Development of Transgenic Tobacco", The Plant Cell, vol. 8, No. 3, Mar. 1996, pp. 349–362.

* cited by examiner

Primary Examiner—Philip Tucker
(74) Attorney, Agent, or Firm—Dilworth & Barrese, LLP

(57) ABSTRACT

The invention pertains to an adduct comprising epoxy groups obtainable by condensation of an epoxy compound and at least a monocyclic phosphite according to Formula 1:

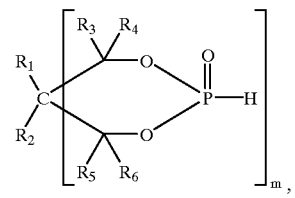

wherein $R_1$ and $R_2$ may be the same or different and represent H or $C_{1-4}$ alkyl and m is 1, optionally, in admixture with a bicyclic phosphite according to Formula 1 wherein $R_1$ and $R_2$ are absent, m is 2, and wherein $R_3$–$R_6$ may be the same or different and represent H or $C_{1-4}$ alkyl.

22 Claims, No Drawings

ADDUCT OF AN EPOXY COMPOUND AND CYCLIC PHOSPHITE

BACKGROUND OF THE INVENTION

The present invention pertains to an adduct of an epoxy compound and a cyclic phosphite, the use of such an adduct in a resin formulation, in synthetic materials, and in particular in prepregs and electrolaminates, and to the synthetic materials, prepregs, and electrolaminates thus obtained.

Phosphorous, flame extinguishing, curable epoxy resins are known per se. Swiss patent application 456,949 discloses that such epoxy resins are obtainable by adding to the formulation a particular quantity of adduct prepared from a 1,2-epoxy-containing compound and dialkyl phosphite or dialkenyl phosphite. Examples of dialkyl phosphite and dialkenyl phosphite are dimethyl phosphite, diethyl phosphite, dipropyl phosphite or dibutyl phosphite, as well as diallyl phosphite or dibutenyl phosphite. In the formation of adducts use is made of epoxy resins having, on average, more than one epoxy function per molecule.

U.S. Pat. No. 3,971,813 describes adducts of hydantoin-containing epoxy resins and phosphites. These epoxy resins contain two or more glycidyl groups per molecule. Specifically, only acyclic phosphites are disclosed in this patent specification (i.e. dimethyl, diethyl, and di-n-butyl phosphite). The drawback to the examples described in this patent specification is that the adducts obtained are not in the pure form, and that volatile components are formed which have to be removed under low pressure on conclusion of the reaction.

The use of the dialkyl phosphite compounds mentioned in the examples results in the formation of oligomeric products of high viscosity. Said high viscosity is the result of the dialkyl phosphite compound being capable of both adding to an epoxy group and transesterifying with two hydroxy groups, which creates very large, branched molecules and may lead to gelling. The alcohol and any residual dialkyl phosphite compound have to be removed from the resulting crude adduct at elevated temperature and reduced pressure. The removal is especially hard when the resin is viscous or the alcohol is high-boiling. Residual alcohol is disadvantageous also because during the curing process, particularly at high temperatures, it will cause the release of yet more alcohol from the chemically bound alkoxy groups, which will interfere objectionably with the curing process or lead to blisters in the cured product.

Polymers prepared from compounds carrying two a-epoxy groups with spiro phosphites, such as 3,9-dioxo-3, 9-diphospha-2,4,8, 10-tetraoxa-spiro[5,5]-undecane, have been disclosed in Japanese patent publication Sho 46-20824. However, the products concerned are high-molecular polymers which do not contain epoxy groups, and which are not cured and used for further processing into products with extra epoxy groups for application in electrolaminates.

SUMMARY OF THE INVENTION

Surprisingly, it was found in the present invention that the transesterification reaction can be avoided completely or virtually completely by having the epoxide compound react to an adduct with cyclic phosphites according to Formula 1:

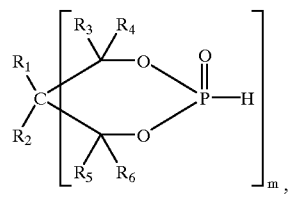

wherein $R_1$ and $R_2$ may be the same or different and represent H or $C_{1-4}$ alkyl, $R_3$–$R_6$ may be the same or different and represent H or $C_{1-4}$ alkyl, and m is 1.

Optionally, the adduct comprising epoxy groups is obtainable by condensation of an epoxy compound and a mixture of a cyclic phosphite according to Formula 1 wherein $R_1$ and $R_2$ may be the same or different and represent H or $C_{1-4}$ alkyl, and m is 1, and a bicyclic phosphite according to Formula 1 wherein $R_1$ and $R_2$ are absent, m is 2, and wherein $R_3$–$R_6$ may be the same or different and represent H or $C_{1-4}$ alkyl.

For that reason, the invention pertains to an adduct comprising epoxy groups obtainable by condensation of an epoxy compound and at least a monocyclic phosphite according to Formula I, or, optionally a mixture of a monocyclic phosphite and a bicyclic phosphate according to Formula I.

The adduct according to this invention has the advantage compared with the prior art that oligomerization, transesterification, and rapid gelling do not occur. Furthermore, the cyclic phosphites have greater thermal stability than acyclic phosphites, so that the reaction with the epoxide compound is less susceptible to high temperatures and long reaction times.

DESCRIPTION OF THE PREFERRED EMBODIMENTS

Particularly preferred are adducts obtained using phosphites wherein m is 1 and $R_1$ and $R_2$ may be the same or different and represent H or $C_{1-2}$ alkyl and wherein $R_3$–$R_6$ represent H. More preferably still, $R_1$ and $R_2$ represent a methyl or ethyl group.

Other suitable phosphites are phosphites according to general formula I, wherein m is 1, $R_1$, $R_2$, $R_3$ and $R_5$ are H, and $R_4$ and R6 are methyl.

Particular preference is given to 5,5-dimethyl-1,3,2-dioxa-phosphorinane-2 oxide as derivative for adduct formation.

In the preparation of the adduct according to the invention use may be made of a di-, tri-, or polyepoxide, or mixtures thereof.

Suitable difunctional epoxy compounds include epoxy resins prepared by reacting aromatic dihydroxy compounds such as bisphenol A, bisphenol S (sulfone bisphenol) or bisphenol F (methylene bisphenol) with epichlorohydrin. As an example may be mentioned the diglycidyl ether of bisphenol A, which is commercially available under the name Epikote 828®.

Also suitable are cycloaliphatic bisepoxides such as 3,4-epoxy-cyclohexyl-methyl-3,4-epoxycyclohexanecarboxylate and aliphatic bisepoxides such as 1, 4-butanediol dig lycidyl ether.

Examples of polyepoxy resins of the phenol type which are suitable for use in the present invention are polyepoxy resins of phenol-formaldehyde novolak or cresol-formaldehyde novolak based on polyglycidyl ethers, polyepoxy resins based on the triglycidyl ether of tris-(p-hydroxyphenol)methane, or polyepoxy resins based on the tetraglycidyl ether of tetraphenylethane. Polyepoxy resins of the amine type such as the polyepoxy resins based on tetraglycidyl methylene diphenyl diamine and triglycidyl isocyanurate are likewise suitable for use. The term "epoxy resin" also encompasses the reaction products of an excess of epoxy-containing compound (e.g., of the aforementioned type) and aromatic dihydro compounds. These dihydroxy compounds can be halogen-substituted. Various other useful types of epoxy resins are described in Clayton A. May, Epoxy Resins, Marcel Dekker, Inc. (1998). Preferably, the epoxy compounds are not hydantoin derivatives containing glycidyl groups.

The adducts are prepared in a melt using an inert, high-boiling solvent such as dimethyl formamide, or in the absence of a solvent at temperatures in the range of 100 to 200° C. Any addition of small quantities of acid catalyst such as tetramethylammonium chloride or tetrabutylphosphonium bromide salts, basic catalysts such as imidazole, 2-ethyl4-methyl imidazole, or metallic sodium will accelerate the reaction.

The molar ratio of monofunctional cyclic phosphite: epoxy groups is smaller than 1 when m is 1 and smaller than 0.5 when m is 2. Adducts without epoxy groups are obtained when the number of epoxy groups and P-H groups is virtually stoichiometric. Such products are not encompassed within the scope of the instant invention. Since it is envisaged to produce adducts in which epoxy groups are present, it is advisable to employ a less than stoichiometric amount of cyclic phosphite. For instance, one mole of epoxy compound containing on average three epoxy groups per molecule in combination with one mole of cyclic phosphite will give an adduct containing on average two epoxy groups and one phosphorous group.

The forming of the adduct during synthesis can be followed by measuring the disappearance of the epoxy groups as a function of time via titration. It was found that the incorporation of cyclic phosphite is complete when per mole of phosphite used, 1 to 1.1 moles of epoxy groups have disappeared.

The disappearance of the phosphite is demonstrated by the disappearance of the characteristic P-H band at 2400 cm$^{-1}$ in the IR spectrum and of the P-H signals at 5.6 and 7.9 ppm in the $^1$H-NMR spectrum. The reaction is halted after complete incorporation of the phosphite into the adduct. There is no transesterification reaction between the (free or incorporated) cyclic phosphite and the hydroxy groups formed by the addition reaction. Thus it was found that adducts in a vacuum of 0.1 mm mercury pressure (13.3 Pa) and at a maximum temperature of 130° C., or at a pressure of 1 atmosphere (0.1 kPa) and 200° C., will lose hardly any material. The gelling time of adducts prepared with cyclic phosphite is much longer than that of the more highly viscous adduct prepared with dialkyl phosphite (which latter adduct also contains more oligomer).

The adducts according to the invention can be processed with suitable curing agents (hardeners) and, optionally, extra epoxy compounds into formulations having flame retardant properties for a wide range of applications including electrolaminates for printed wiring boards (PWBs). The invention therefore also pertains to a resin formulation, characterized in that it comprises the previously mentioned adduct or an adduct comprising epoxy groups obtainable by condensation of an epoxy compound and a cyclic phosphite according to Formula 1 wherein $R_1$ and $R_2$ are absent, $R_3$–$R_6$ may be the same or different and represent H or $C_{1-4}$ alkyl, and m is 2, a hardener and, optionally, extra epoxy compound and catalyst.

The well-known glass-reinforced and epoxy-containing laminates for PWBs generally have been rendered flame retardant by the incorporation of brominated compounds. For instance, the most commonly used FR-4 laminate contains an epoxy resin prepared by reacting tetrabromobisphenol A with an excess of diglycidyl ether of bisphenol A. However, the drawback to such adducts is that on combustion the toxic dioxin is formed.

The adducts found in the present invention make it possible to formulate bromine-free epoxy compounds which in processing and properties terms constitute a favorable alternative to the bromine-containing epoxy compounds in the electrolaminates industry.

The resin formulation consists of the adduct obtainable from the afore-mentioned mono-cyclic or bicyclic phosphite, or from a mixture thereof, a hardener, and, optionally, additional epoxy compound and catalyst. A phosphorus content of 2 to 6% is required to render the cured formulation flame retardant. Using nitrogenous reactive compounds in the formulation, e.g., guanamine (such as benzoguanamine) and (iso)cyanurate derivatives, makes for an extra contribution to the flame retardance.

Suitable hardeners are known to the skilled person. They include polyhydric aromatic compounds, cyclic anhydrides, and amines. Preferably, the thardeners do not contain P-H groups. Examples of polyhydric aromatic compounds are phenol/formaldehyde novolak and cresol/formaldehyde novolak resins, as well as resorcinol, bisphenol A, and sulfone bisphenol. Examples of cyclic anhydrides are cyclic aromatic anhydrides such as phthalic anhydride, tetrabromophthalic anhydride, cycloaliphatic anhydrides such as hexahydrophthalic anhydride, and copolymers of maleic anhydride and styrene. Examples of amines are dicyanodiamide, diphenyl guanidine, benzoguanamine, and aromatic amines such as methylene dianiline and 1,3,5-tris-(3-amino4-alkylphenyl)-2,4,6-trioxo-hexahydrotriazine.

As suitable catalysts for adjusting the reactivity of the resin formulation may be mentioned imidazoles, more particularly, alkyl-substituted imidazoles such as 2-methylimidazole and 2-ethyl-4-methylimidazole, as well as tertiary amines such as benzyl dimethylamine.Also suitable for use are cationic catalysts such as boron trifluoride ethylamine complex.

The quantity of catalyst employed is dependent on the chemical composition of the resin formulation, but will generally be in the range of 0.01 to 5 per cent by weight, calculated on the overall weight of the solid resin components. The usual additives may be added to the resin formulation according to the invention, e.g., dyes, pigments, thixotropic agents, flow regulators, and stabilizers. If so desired, additional inorganic solid flame extinguishers such as aluminum trihydrate or magnesium hydroxide or organic solid or liquid flame extinguishers such as salt of melamine with phosphoric acid and aromatic phosphonate oligomers may be added to further increase flame retardance. As is disclosed in PCT/EP92/02795, interpenetrating polymer network technology makes it possible to use triallyl(iso) cyanurate polymerizable under the influence of radicals as a second network in addition to the epoxy network to increase flame retardance.

Generally, organic solvents are used when preparing the resin formulation for electrolaminates. Suitable solvents are glycol ethers such as propylene glycol monomethyl ether, N,N-dimethyl formamide, and ketones such as methylethyl ketone and acetone, or mixtures thereof.

Laminates for the electronics industry (notably for PWBs) are commonly made by impregnating a supporting or reinforcing fabric with a resin solution, removing the solvent from the impregnated fabric in a tower with heating, and partially curing the resin. Such an impregnated fabric is usually referred to as a prepreg. Several prepregs together with one or more layers of copper laminated with heat and pressure will give an electrolaminate which can be made into a PWB by means of well-known printing and etching processes.

The resin formulations containing the adduct according to the invention are suited to be used for impregnating, say, fabric, unidirectionally laid bundles, and cloth made of a wide range of materials such as glass, quartz, carbon, aramid, and boron fibres. They are particularly suited to be used in the manufacture of electrolaminates.

In addition, the resin formulations according to the invention, which may be free of solvents or not, can be used to make epoxy resin-containing glue, coating, potting resin, embedding resin, encapsulating resin, sheet molding compounds, and bulk molding compounds.

Also, the resin formulations according to the invention can be used to make composites for, say, the construction, aviation, and motor industries. Composites suitable for this purpose can be made in a known manner, e.g., by impregnating reinforcing material with molten or dissolved resin or by means of resin transfer molding, filament winding, pultrusion or RIM (reaction injection molding).

The adducts according to this invention can be modified in conventional ways familiar to the skilled person, e.g., by reacting the epoxy groups with carboxylic acids polymerizable under the influence of radicals such as (meth)acrylic acid. In this way phosphorous vinyl esters are obtainable which can be cured under the influence of radicals to form a flame retardant network.

The invention will be illustrated with reference to the following examples below.

EXAMPLE 1

In a reaction flask equipped with a reflux condenser 52.8 g of a liquid, viscous phenol-formaldehyde novolak epoxy resin having an average epoxy functionality of 3.6 and an epoxy equivalent weight (EEW) of 176 were combined with 16.5 g of freshly distilled 5,5-dimethyl-1,3,2-dioxaphosphoin-ane-2-oxide (boiling point 110° C. at 0.5 mm mercury pressure (66.65 Pa), melting point 55° C.). With stirring and under a static nitrogen atmosphere, the reaction mixture was heated in 5 min to 120° C., whereupon 0.1 ml of a 40%-solution of tetramethyl ammonium chloride in methanol was added. The clear reaction mixture was then heated in 40 min to 161° C. and kept at this temperature for 140 min. After a total reaction time of 185 min the pale yellow mass was cooled and dissolved in methylethyl ketone (MEK) to a 66.6% (w/w) low-viscous, clear solution. The absence of the 2400 cm$^{-1}$ band from the infrared spectrum showed that the phosphite had been incorporated completely. On the end product having an EEW of 395 and an epoxy content of 2.53 eq/kg the gelling time was determined at 171° C. with slow stirring with a wooden stick. After 4 h the end product had not yet gelled, showing that the product, unlike the product from Reference example 2, did not tend to rapid network formation. Thermogravimetric analysis (TGA) of the solid end adduct, performed under nitrogen at a heating rate of 10° C./min, gave 0.9% of volatile material at 200° C. and 3% at 250° C.

EXAMPLE 2 (REFERENCE EXAMPLE)

In a manner analogous to that described in Example 1 52.8 g of the phenolformaldehyde riovolak epoxy resin having an average epoxy functionality of 3.6 and an epoxy equivalent weight of 176 were combined with 15.2 g of diethyl phosphite (boiling point 51° C. at 2 mm mercury pressure (0.27 kPa)). With stirring and under a static nitrogen atmosphere, the reaction mixture was heated in 5 min to 123° C. After the addition of 0.1 ml of a 40%-solution of tetramethyl ammonium chloride in methanol, the clear reaction mixture was finally heated to 161° C. and kept at this temperature for 200 min. The ethanol formed during the reaction was distilled off under passage of nitrogen at 161° C. in 30 min, after which the mass was cooled and 60.1 g of solid end product with a found phosphorus content of 5.51% and an epoxy content of 2.75 eq/kg were obtained. Infrared analysis showed the absence of diethyl phosphite. A 66.6%-solution of the adduct in MEK was found to be high-viscous. The gelling time of the solid adduct at 171° C. was 13 min, which is substantially shorter than the gelling time of the adduct from Example 1. TGA of the solid end adduct gave 1.3% of volatile material at 200° C. and 3.5% at 250° C.

EXAMPLE 3

In a flanged flask 138.3 g of finely powdered and dried triglycidyl isocyanurate having an EEW of 108 were combined with 70.2 g of freshly distilled 5,5-dimethyl-1,3,2-dioxaphosphorinane-2-oxide. The mixture was heated in 45 min to 126° C. To the mostly molten material was added, with stirring, 0.1 ml of a 40%-solution of tetramethyl ammonium chloride in methanol, the temperature of the mixture gradually being increased over one hour to 154° C. After 40 min of stirring at this temperature the clear mixture had turned yellow. The mass was then poured out and cooled on thick aluminum foil. The EEW of the adduct was 286, the phosphorus content 6.9%. The $^1$H-NMR spectrum in DMSO-d$_6$ showed that the P-H bands at 5.6 and 7.9 ppm (typical of the phosphite) had disappeared. The solids content was determined at 171° C. over a period of 3 h, without any loss of solid material being observed.

EXAMPLE 4

12 g of a 50%-solution (w/w) of the adduct according to Example 3 in 1-methoxy-2-propanol were mixed with 5.5 g of diglycidyl ether of bisphenol A Epikote 828 (Epikote 828 [Shell], EEW 187), 4.8 g of a 10%-solution of dicyanodiamide in N,N-dimethyl formamide, and 48 mg of 2-methylimidazole. The solution was poured into aluminum cups and subjected to the following successive temperatures in a forced-circulation air oven: 1 h at 80° C., 1 h at 120° C., 30 min at 150° C., and 1 h at 171° C. On the about 1 mm thick, cured resin slices a Tg of 130° C. was measured using thermomechanical analysis (TMA, range 20 to 250° C., 10° C./min under nitrogen). Post-curing for 2 h at 200° C. yielded the same Tg.

EXAMPLE 5

To 394 g of a 50%-solution of the adduct according to Example 3 in 1-methoxy-2-propanol were successively added 118.2 g of Epikote 1001 (bisphenol A diglycidyl ether, EEW 540), 63 g of Epikote 828, 15.8 g of diphenyl guanidine, 47.6 g of acetone, 39 g of a 10%-solution of 2-methyl-imidazole in 1-methoxy-2-propanol, and a solution of 1.5 g of SMA3000 (styrene-maleic acid copolymer [Elf Atochem] having an average MW of 2840D) in 1.5 g of acetone. The viscosity of the solution was 152 mPa.s, the gelling time at 171° C. was 8 min. After manual impregnation, this resin and glass cloth (type 7628) was made into prepregs in a forced-circulation air oven at 171° C. The resin content and the material gelling time of the tack-free prepregs were 45% and 285 sec, respectively, measured in accordance with IPC.

Eight stacked prepregs were molded for 60 min in an autoclave at a pressure of 1.5 kPa and a temperature of 171° C. Heating and cooling took place at a rate of 5° C./min. In this way laminate coated on both sides with copper (1 ounce (28.35 g), electrodeposited type) was obtained, as well as uncoated laminate having a thickness in the range of 1.50 to 1.60 mm. The Tg of the laminates as determined by TMA (thermomechanical analysis) and DSC (differential scanning calorimetry) was about 128° C. The fire retardance, determined in accordance with UL-94, was in conformity with class V-1.

EXAMPLE 6

Epikote 828 (617 g) and pure 5,5-dimethyl-1,3,2-dioxaphophorane-2-oxide (151 g) were heated to 140° C., and 4.7 g of a 20%-solution of imidazole in 1-methoxy-2-propanol were added. The mixture was heated to 150° C. in 5 min and kept at that temperature for 3.5 h, after which the EEW was 380. The mixture was cooled to 125° C., and 235.5 g of 1-methoxy-2-propanol and 66.8 g of benzoguanamine were added. The mixture was heated to 140° C. and a reaction product was obtained, of which the gelling time measured at 171° C. was getting shorter as function of the reaction time. After about 2 h, the solution was cooled to room temperature and the gelling time was 18 min. The gelling time of a 78%-solution of the adduct did not change over a period of 1 month.

A resin was prepared from 640 g of a 70%-solution of this adduct in 1-methoxy-2-propanol, 138 g of a 10%-solution of dicyanodiamide in DMF, 75 g of MEK, and 3.7 g of a 10%-solution of 2-methylimidazole in 1-methoxy-2-propanol. The resin having a viscosity of 150 mPa.s was made into prepregs with glass cloth (type 7628) at 165° C. The resin content and the material gelling time of the tack-free prepregs were 43% and 200 sec, respectively, measured in accordance with IPC.

In a manner analogous to that of Example 5 laminates having a thickness of 1.50 mm were prepared. The Tg of the laminates as determined by DSC was 120° C. The fire retardance, determined in accordance with UL-94, was in conformity with class V-1.

EXAMPLE 7

3,9-Dioxo-3,9-diphospha-2,4,8,10-tetraoxa-spiro[5.5]undecane was prepared as follows. Under stirring and a nitrogen atmosphere a suspension of 68 g of pentaerythitol, 152 g of diethylphosphite, and 73 g of water-free tetraline was heated to 135° C. At 135° C., 55% of the theoretical amount of ethanol were removed from the reaction mixture over a period of 3 h. The pressure was diminished slowly to 10 kPa and more ethanol was removed at 135° C. After cooling to 80° C., 60 g of methanol were added after which the methanol layer with the product was separated from the tetraline layer. After evaporation at a 95° C. and a pressure of 0.2 kPa, 100 g of a viscous product were obtained, which crystallized on standing at room temperature.

EXAMPLE 8

Epikote 828 (404 g) was heated to 110° C. and 110 g of a 90%-solution of 3,9-dioxo-3,9-diphospha-2,4,8,10-tetraoxa-spiro[5.5]undecane in DMF, heated to 70° C., were added after which the mixture was heated to 130° C. 0.25 g of a 20%-solution of imidazole in 1-methoxy-2-propanol were added. The mixture was heated to 140° C. and kept at that temperature until an EEW of 460 was reached, after which 150 g of 1-methoxy-2-propanol were added as extra solvent.

A resin was prepared from 469 g of the solution and 145 g of a 10%-solution of dicyanodiamide in DMF, and 231 g of MEK to a resin solution having a viscosity of 140 mPa.s and a gelling time of 200 sec. The resin was made into prepregs with glass cloth (type 7628) at 160° C. The resin content and the material gelling time of the tack-free prepregs were 43% and 120 sec, respectively, measured in accordance with IPC.

In a manner analogous to that of Examples 5 and 6 laminates having a thickness of 1.52 mm were prepared. The Tg of the laminates as determined by DSC was 130° C. The fire retardance, determined in accordance with UL-94, was in conformity with class V-1.

What is claimed is:

1. An adduct comprising epoxy groups obtainable by condensation of an epoxy compound and at least a monocyclic phosphite according to Formula 1:

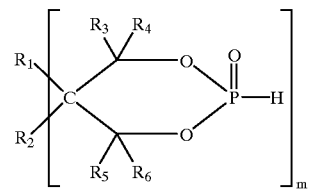

wherein $R_1$ and $R_2$ may be the same or different and represent H or $C_{1-4}$ alkyl, $R_3$–R6 may be the same or different and represent H or $C_{1-4}$ alkyl $R_3$–$R_6$ may be the same or different and represent H or $C_{1-4}$ alkyl, and m is 1.

2. The adduct of claim 1 wherein $R_1$ and $R_2$ both represent a methyl or ethyl group, and $R_3$–$R_6$ are H.

3. The adduct of claim 1 wherein $R_1$ and $R_2$ and $R_3$ and $R_5$ are H, and $R_4$ and $R_6$ are methyl.

4. The adduct of claim 1 wherein the monocyclic phosphite is 5,5-dimethyl-1,3,2-dioxaphosphorinane-2-oxide.

5. An adduct comprising epoxy groups obtainable by condensation of an epoxy compound and a mixture of:
   a) a monocyclic phosphite according to Formula 1:

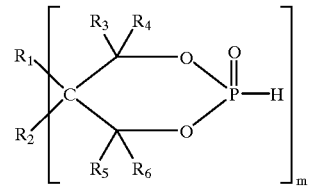

wherein $R_1$ and $R_2$ may be the same or different and represent H or $C_{1-4}$ alkyl, $R_3$–R6 may be the same or different and represent H or $C_{1-4}$ alkyl, and m is 1; and,
   b) a bicyclic phosphite according to Formula 1 wherein $R_1$ and $R_2$ are absent, m is 2, and wherein $R_3$–R6 may be the same or different and represent H or $C_{1-4}$ alkyl.

6. A resin formulation, characterized in that it comprises the adduct of claim 5 or an adduct comprising epoxy groups obtainable by condensation of an epoxy compound and a bicyclic phosphite according to Formula 1 wherein $R_1$ and $R_2$ are absent, $R_3$–$R_6$ may be the same or different and represent H or $C_{1-4}$ alkyl, and m is 2, and in addition includes a hardener and, optionally, extra epoxy compound and catalyst.

7. A synthetic material, characterized in that it comprises the adduct of claim 1.

8. A prepreg or electrolaminate, characterized in that it comprises the adduct of claim 1.

9. A process for preparing the adduct of claim 5, characterized in that a monocyclic phosphite according to Formula 1;

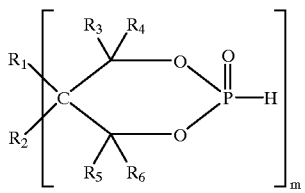

wherein $R_1$ and $R_2$ may be the same or different and represent H or $C_{1-4}$ alkyl, $R_3$–R6 may be the same or different and represent H or $C_{1-4}$ alkyl, and m is 1; and, a bicyclic phosphite according to Formula 1 wherein $R_1$ and $R_2$ are absent, $R_3$–R6 may be the same or different and represent H or $C_{1-4}$ alkyl, and m is 2, and an epoxy compound are melt condensed using an inert, high-boiling solvent, or in the absence of solvent, with the molar ratio monocyclic phosphite a): epoxy groups being smaller than 1, and the molar ratio bicyclic phosphite b) : epoxy groups being smaller than 0.5.

10. The adduct of claim 5 wherein $R_1$ and R2 both represent a methyl or ethyl group when m is 1, and R3–$R_6$ are H.

11. The adduct of claim 5 wherein $R_1$ and R2 when m is 1, and $R_3$ and $R_5$ are H, and R4 and R6 are methyl.

12. The adduct of claim 5 wherein the monocyclic phosphite is 5, 5-dimethyl-1,3,2-dioxaphosphorinane-2-oxide.

13. A synthetic material, characterized in that it comprises the resin formulation of claim 6.

14. A prepreg or electrolaminate, characterized in that it comprises the resin formulation of claim 6.

15. A resin formulation, characterized in that it comprises at least one adduct selected from the group consisting of the adduct of claim 2 and a different adduct comprising groups obtainable by condensation of an epoxy compound and a bicyclic phosphite according to Formula 1 wherein $R_1$ and $R_2$ are absent, $R_3$–R6 may be the same or different and represent H or $C_{1-4}$ alkyl, and m=2, and in addition includes a hardener and, optionally, extra epoxy compound and catalyst.

16. A resin formulation characterized in that it comprises at least one adduct selected from the group consisting of the adduct of claim 3 and an adduct comprising epoxy groups obtainable by condensation of an epoxy compound and a bicyclic phosphite according to Formula 1 wherein $R_1$ and $R_2$ are absent, $R_3$–$R_6$ may be the same or different and represent H or $C_{1-4}$ alkyl, and m=2, and in addition includes a hardener and, optionally, extra epoxy compound and catalyst.

17. A resin formulation characterized in that it comprises at least one adduct selected from the group consisting of the adduct of claim 4 and an adduct comprising epoxy groups obtainable by condensation of an epoxy compound and a bicyclic phosphite according to Formula 1 wherein $R_1$ and $R_2$ are absent, $R_3$ –$R_6$ may be the same or different and represent H or $C_{1-4}$ alkyl, and m=2, and in addition includes a hardener and, optionally, extra epoxy compound and catalyst.

18. A synthetic material comprising the adduct of claim 1.

19. The synthetic material of claim 18 wherein the synthetic material is selected from the group consisting of prepeg and electrolaminate.

20. A synthetic material comprising the resin formulation of claim 6.

21. The synthetic material of claim 20 wherein the synthetic material is selected from the group consisting of prepeg and electrolaminate.

22. A process for preparing the adduct of claim 5, the process comprising melt condensing the phosphite mixture of claim 5 and an epoxy compound in the presence or absence of an inert high boiling solvent, wherein the molar ratio of monocyclic phosphite a) to epoxy groups is smaller than 1 and the molar ratio of bicyclic phosphite b) to epoxy groups is smaller than 0.5.

* * * * *